US005846530A

United States Patent [19]
Soon-Shiong et al.

[11] Patent Number: 5,846,530
[45] Date of Patent: Dec. 8, 1998

[54] MACROCAPSULES PREPARED FROM CROSSLINKABLE POLYSACCHARIDES, POLYCATIONS AND/OR LIPIDS AND USES THEREFOR

[75] Inventors: Patrick Soon-Shiong; Neil P. Desai; Paul A. Sandford; Roswitha A. Heintz, all of Los Angeles; Soebianto Sojomihardjo, Pasadena, all of Calif.

[73] Assignee: Vivorx, Inc., Santa Monica, Calif.

[21] Appl. No.: 475,175

[22] Filed: Jun. 7, 1995

Related U.S. Application Data

[60] Division of Ser. No. 232,054, filed as PCT/US92/09364, Oct. 29, 1992, which is a continuation-in-part of Ser. No. 784,267, Oct. 29, 1991, abandoned.

[51] Int. Cl.$^6$ ............................. A61K 9/62; A61K 9/64; A61K 9/56
[52] U.S. Cl. ........................ 424/93.7; 424/460; 424/461; 424/462; 424/486; 424/487; 424/488; 424/93.1; 522/87; 522/88
[58] Field of Search ........................... 428/321.5; 522/87; 522/88; 424/460, 461, 462, 93.7, 486, 487, 488

[56] References Cited

U.S. PATENT DOCUMENTS

| | | | |
|---|---|---|---|
| 4,353,888 | 10/1982 | Sefton | 424/25 |
| 4,450,233 | 5/1984 | Mimura et al. | 435/178 |
| 4,806,355 | 2/1989 | Goosen et al. | 424/424 |
| 5,084,350 | 1/1992 | Chang et al. | 428/402.2 |
| 5,158,881 | 10/1992 | Aebischer et al. | 435/182 |
| 5,334,640 | 8/1994 | Desai et al. | 524/56 |
| 5,529,914 | 6/1996 | Hubbell et al. | 435/182 |
| 5,545,423 | 8/1996 | Soon-Shiong et al. | 424/484 |
| 5,550,050 | 8/1996 | Holland et al. | 435/240.2 |

FOREIGN PATENT DOCUMENTS

| | | |
|---|---|---|
| 190215 | 5/1986 | European Pat. Off. . |
| 0216453-A2 | 3/1987 | European Pat. Off. . |
| 0251905-A2 | 8/1987 | European Pat. Off. . |
| 0265116-A2 | 4/1988 | European Pat. Off. . |
| 54-128482 | 10/1979 | Japan ..................... 522/88 |

OTHER PUBLICATIONS

Abuchowski et al., "Alteration of Immunological Properties of Bovine Serum Albumin by Covalent Attachment of Polyethylene Glycol" *J. Biol. Chem.* 252:3578–3581 (1977).

Braun et al., "The encapsulation of pancreatic islets. Investigation of insulin secretion and content in vitro" *Biochim. Acta* 44:143–147 (1995).

Chang, "Microencapsulation and Artificial Cells" *Humana Press*, Clifton, NJ, pp. 4–26 (1984).

Chang, "Artificial Cells in Medicine and Biotechnology" *Humana Press*, 10: 4–24 (1984).

Darquy and Reach "Immunoisolation of pancreatic B cells by microencapsulation" *Diabetologia* 28:776–780 (1985).

Decker and Moussa, "Real–Time Kinetic Study of Laser–Induced Polymerization" *Macromolecules* 22:4455–4461 (1989).

Desai and Hubbell "Solution technique to incorporate polyethylene oxide and other water–soluble polymers into surfaces of polymeric biomaterials" *Biomaterials* 12:144–153 (1991).

Dupuy et al., "Agarose Beads in Paraffin Oil as Interfaces to Encapsulate Living Cells. Tests of function with Islets of Langerhans" *Artif. Organs* 11:314 (1987).

Dupuy et al., In situ polymerization of a microencapsulating medium round living cells *Journal of Biomedical Materials Research* 22:1061–1070 (1988).

Eaton, David F., "Dye Sensitized Photopolymerization" *Advances in Photochemistry* 13:427–487 (1986).

Gharapetian et al., "Encapsulation of Viable Cells Within Polyacrylate Membranes" *Biotech. Bioeng.* 28:1595–1600 (1986).

Goosen et al., "Optimization of Microencapsulation Parameters: Semipermeable Microcapsules as a Bioartificial Pancreas" *Biotechnol. Bioeng.* 27:146–150 (1985).

Harris, J. Milton, "Laboratory Synthesis of Polyethylene Glycol Derivatives" *JMS–Rev. Macromol. Chem. Phys.* C25(3):325–373 (1985).

Harris et al., "Synthesis and Characterization of Poly(ethylene Glycol) Derivatives" *J. Polym. Sci., Polym. Chem. Ed.* 22:341–352 (1984).

Hoyle et al., "Laser–Pulsed Photopolymerization of Methyl Methacrylate: The Effect of Repetition Rate" *Macromolecules* 22:3866–3871 (1989).

Iwata et al., "Evaluation of Microencapsulated Islets in Agarose Gel as Bioartificial Pancreas by Studies of Hormone Secretion in Cultrue and by Xenotransplantation" *Diabetes* 38(1):224–225 (1989).

Karu, T. I., "Effects of Visible Radiation on Cultured Cells" *Photochem. and Photobiol.* 52:1089–1098 (1990).

Lanza et al., "Large–Scale Canine and Human Islet Isolation Using a Physiological Islet Purification Solution" *Diabetes* 39:309A (1990).

(List continued on next page.)

*Primary Examiner*—Susan W. Berman
*Attorney, Agent, or Firm*—Stephen E. Reiter; Gregory P. Raymer; Gray Cary Ware & Freidenrich

[57] ABSTRACT

The present invention relates to a new form of biocompatible materials (e.g., lipids, polycations, polysaccharides) which are capable of undergoing free radical polymerization, e.g., by using certain sources of light; methods of modifying certain synthetic and naturally occurring biocompatible materials to make polymerizable microcapsules containing biological material coated with said polymerizable materials, composites of said polymerizable materials, methods of making microcapsules and encapsulating biological materials therein, and apparatus for making microcapsules containing biological cells (particularly islets of Langerhans) coated with polymerizable alginate or with a composite thereof (e.g., alginate and PEG). The present invention also relates to drug delivery systems relating to the foregoing, as well as bioadhesives and wound dressings made utilizing the foregoing technology.

22 Claims, No Drawings

OTHER PUBLICATIONS

Lim and Sun, "Microencapsulated Islets as Bioartificial Endocrine Pancreas" *Science* 210:908–910 (1980).

Mathias et al., "Synthesis and Polymerization of Mono–and Divinyl Ethers of Oligooxyethylenes" *J. Polym. Sci., Polym. Lett. Ed.* 20:473–479 (1982).

Moe et al., "Covalently cross–linked sodium alginate beads" *Food Hydrocolloids* 5:119–123 (1991).

Morrison and Boyd, "Organic Chemistry" *Organic Chemistry, Allyn and Bacon*, pp. 756–757 (1973).

Pitha et al., "Detergents Linked to Polysaccharides: Preparation and Effects on Membranes and Cells" *Eur. J. Biochem.* 94:11–18 (1979).

Sefton et al., "A HEMA–MMA Copolymer for the Microencapsulation of Mammalian Cells" *Polymer Preprints* 31:217–218 (1990).

Smidsrod and Skjak–Braek, "Alginate as immobilization matrix for cells" *Trends in Biotechnology* 8:71–78 (1990).

Soon–Shiong et al., "Islet Purification by a Novel Immunomicrosphere Cell Depletion Technique" *Transplantation Proceedings* 22(2):780–781 (1990).

Soon–Shiong et al., "An Immunologic Basis for the Fibrotic Reaction to Implanted Microcapsules" *Transplantation Proceedings* 23(1):758–759 (1991).

Wu, David S., "Optical–scanner design impacts rapid laser prototyping" *Laser Focus World* pp. 99–106 (Nov. 1990).

MACROCAPSULES PREPARED FROM CROSSLINKABLE POLYSACCHARIDES, POLYCATIONS AND/OR LIPIDS AND USES THEREFOR

This application is a divisional of U.S. application Ser. No. 08/232,054, filed as PCT/US92/09364 Oct. 29, 1992, now pending; which is in turn a continuation-in-part of U.S. application Ser. No. 07/784,267, filed Oct. 29, 1991, now abandoned.

The present invention relates to a new form of biocompatible materials (including lipids, polycations, and polysaccharides) which are capable of undergoing free radical polymerization. The invention also relates to methods of modifying certain synthetic and naturally occurring biocompatible materials to make polymerizable microcapsules containing biological material. The invention also relates to composites of said polymerizable materials, methods of making microcapsules and encapsulating biological materials therein, and apparatus for making microcapsules containing biological cells. The present invention also relates to drug delivery systems relating to the foregoing, and bioadhesives and wound dressings made utilizing the foregoing technology.

BACKGROUND OF THE INVENTION

Over the past 10 to 15 years various combinations of ionic polymers have been tested and utilized for microencapsulation of live cells and tissues. The most widely accepted material of the prior art is polylysine alginate, particular for in vivo applications. (Dupuy, 1988(12.); Chang, 1984(3.); Braun,1985(2.); Goosen, 1985(15.), Darquy, 1985(14. )). However, these polymers are water soluble in the form known in the prior art, and therefore have been considered to be of limited long-term stability.

Polysaccharides such as alginates have been used extensively in recent years in the food, cosmetics, pharmaceutical and biomedical industries (Smidsrød and Skjak-Bræk, 1990 (28.)). In the pharmaceutical and biomedical industries, their gel forming properties in the presence of multivalent cations have been exploited for the microencapsulation of cells and tissue and controlled release of drugs.

It is the combination of multivalent (generally divalent) cations, such as calcium, with the alginate, which provides the mechanical stability of the ionically crosslinked gel. However, in the physiological environment (e.g., in the transplantation of microencapsulated islets or for drug release) extracellular concentrations of monovalent cations (such as sodium ions) exceed the concentration of divalent cations (such as calcium). Under such conditions, these gels tend to lose their mechanical stability over the long term due to diffusion, leading to exchange of divalent cations for monovalent cations in the physiological fluid.

In an effort to improve the mechanical stability of these gels, chemical modifications of the alginates have been proposed (Moe et al., 1991(24.)) utilizing covalent rather than ionic crosslinking. These techniques involve the use of reagents, reaction conditions and relatively long reaction periods which, if used for the encapsulation of living tissue, are likely to prove toxic and even fatal.

Researchers have used alginate gels for the immunoisolation of transplanted tissue to treat insulin dependent diabetes (Lim and Sun, 1980(22.)). Alginates containing higher fractions of α-L-guluronic acid residues (G-content) have been determined to be more biocompatible (i.e., they do not induce a cytokine response from monocytes) than those containing a larger fraction of β-D mannuronic acid residues (M-content; see Soon-Shiong et al.,. 1991(30.)). Thus, implanted gels of alginates containing a high M-content, when implanted in rats, show extensive fibrous overgrowth at 3 weeks while high G-content alginates show no fibrous overgrowth for the same implantation period.

Thus, it would be desirable to be able to provide alginates which are covalently polymerized and are substantially more stable under physiological conditions than are prior art alginate compounds and implantation systems with alginate coats. It would also be desirable to provide alginates which may be rapidly polymerized, relative to the rate of crosslinking with prior art ionically crosslinked systems.

Previous attempts to make stable polymers for microencapsulation have met with limited success. Many of the more stable polymers appear to be relatively cytotoxic due in large part to the chemical reactivity of the monomer precursors used.

Other biocompatible materials such as lipids, polycations and other polysaccharides (e.g., hyaluronic acid and chitosan) have been used or suggested for use in microencapsulation applications, but are subject to similar drawbacks of slow and relatively unstable crosslinking. The resultant polymers suffer from the same disadvantages as described above. It would, therefore, be desirable to modify such materials so that they polymerize more rapidly and remain mechanically more stable under typical physiological conditions of use.

Attempts to improve stability of capsule membranes include the use of water-insoluble polymers for microencapsulation such as acrylate co-polymers and methacrylate co-polymers (Gharapetian, et al., 1986(14.); Sefton, et al., 1987(27.); Iwata, 1989(19.); Dupuy, 1987(11.)) and photopolymerized polyacrylamide (Dupuy, 1988(12.)). These methods suffer from cytotoxicity of the materials or organic solvents associated with these polymers, as well as long-term in vivo lack of biocompatibility of these water-insoluble polymers.

It has recently been demonstrated that alginates containing higher fractions of α-L guluronic acid residues (G-content) are biocompatible since they do not induce cytokines responsible for fibroblast proliferation (Soon-Shiong, 1991(30.)). Furthermore, encapsulated islets in these high G-content alginate gels successfully reverse diabetes in spontaneous diabetic dogs. Long-term function of these ionically crosslinked gels, however, has been hampered by chemical and possibly mechanical disruption of the alginate-polylysine membrane, resulting in rejection and fibrous overgrowth of the exposed allograft.

The ideal encapsulation system requires a gel entrapment system of materials which are mild and non-cytotoxic to living materials, provides an immunoprotective barrier to the recipient's immune system, allows adequate diffusion of nutrients through the barrier to ensure cell survival, is biocompatible, and finally is chemically and mechanically stable.

The alginate-polylysine entrapment system using high G alginates meets most of these criteria, except for limited stability of the membrane. The present disclosure describes materials and methods which increase the mechanical stability of the ionically crosslinked alginate gel system either by increasing the strength of the ionic bonds involved in the gellation process, or by providing material resulting in covalent crosslinkage.

SUMMARY OF THE INVENTION

The present invention relates to a new form of biocompatible materials, including lipids, polycations, polysaccharides, and particularly alginate, chitosan and hyaluronic acid, which are capable of undergoing free radical polymerization, e.g., by using certain sources of energy, such as light; methods of modifying certain synthetic and naturally occurring biocompatible materials to make polymerizable microcapsules containing biological material therein, composites of said polymerizable materials, methods of making said microcapsules and encapsulating biological materials therein, and apparatus for making microcapsules containing biological cells (particularly islets of Langerhans) coated with said polymerizable material or with composites thereof, e.g., alginate and PEG. The present invention also relates to drug delivery systems relating to the foregoing, as well as bioadhesives and wound dressings made utilizing the foregoing technology.

Accordingly, a process has been developed for the crosslinking of alginates and other polysaccharides, polycations and lipids under innocuous conditions at physiological pH and reaction times in milliseconds. Such conditions will ensure the survivability of the living tissue involved. New biomaterials which are subject to polymerization under such innocuous conditions have also been developed. In accordance with the present invention, biological materials encapsulated with the above-described polymerizable biocompatible materials have also been developed.

This process involves the chemical modification of polysaccharides (or other polymers) with polymerizable acrylate or acrylate-like groups. A water soluble free radical initiator (e.g., a photosensitizer) is then added to this modified polymer solution in an aqueous buffer containing the cells in suspension. The cell-containing suspension is then extruded through a nozzle or emulsified to produce tiny droplets that can be rapidly crosslinked in the presence of suitable free radical initiating conditions (e.g., exposure to a suitable light source).

By chemical modification of alginate, for example, a unique biomaterial which has the dual capacity to undergo both ionic and covalent crosslinking has been developed. By controlling the reactants and process of modification, the degree of ionic and/or covalent cross-linking can be modified. Furthermore, ionic bonding of this novel modified alginate can be strengthened by the use of cations with high affinity for the anionic groups available, or by increasing the negative charge density of naturally occurring alginate. These novel alginate materials, with dual capacities of ionic and covalent crosslinking facilitate the invention methods of encapsulating biological material and biologically active (or pharmaceutically active) agents.

The present invention provides an encapsulation system which gels rapidly under conditions which are innocuous and gentle to living cells. The encapsulation system of the present invention is more stable than many prior art systems because the compounds are covalently polymerized, in addition to merely being ionically crosslinked. Covalent polymerization can be carried out according to the invention using UV or visible light, so that the polymerization is specific, localized and rapid. Therefore, the detrimental effects of capsule instability on the encapsulated biologically active material, as well as on the recipient, when capsules are introduced into the body under physiological conditions (i.e., the loss of immunoprotection for the encapsulated biologically active material and the induction of fibrosis) are minimized.

Microcapsules or macrocapsules prepared by the invention process are useful for a variety of therapeutic applications, such as the encapsulation of islets of Langerhans for the treatment of diabetes; encapsulation of dopamine secreting cells for the treatment of Parkinsons disease; encapsulation of hepatocytes for the treatment of liver dysfunction; encapsulation of hemoglobin to create artificial blood; encapsulation of biological materials for diagnostic purposes; encapsulation of biological materials for in vivo evaluation of the effects of such biological materials on an organism, and conversely, the effects of the organism on the materials; encapsulation of tumor cells for evaluation of chemotherapeutic agents; encapsulation of human T-lymphoblastoid cells sensitive to the cytopathic effects of HIV; and the like.

The invention compositions are also useful for the preparation of a drug delivery vehicle for the measured release of therapeutic agents; for the encapsulation of biomedical devices for implantation (to increase the stability and biocompatibility of the devices); for the preparation of materials which prevent adhesion; for the preparation of bioadhesives; for the preparation of dressings useful in wound healing; and the like.

In another aspect of the present invention, there is provided a retrievable system for microencapsulated cells, wherein microencapsulated cells (made in accordance with the present invention) are disposed in a "tea bag," tube or cylinder which may also be made from the materials of the present invention. The retrievable system permits diffusion of the biologically active material provided or made therewithin, provides biocompatibility with a host in which the system is disposed, and retrievability of the system, while providing immunoprotection of the biomaterial within the retrievable system.

DETAILED DESCRIPTION OF THE INVENTION

Starting with either a naturally occurring or synthetic (chemically modified and/or commercially available) polysaccharide, lipid or polycation, it has been discovered that such materials can be modified to impart a functionality capable of covalent crosslinking by free radical polymerization. Such free radical polymerization may be initiated by light or other forms of energy using appropriate initiators. While most of the examples herein refer to photopolymerization, a person skilled in the art will recognize that other methods of initiating polymerization are possible including thermal, ultrasonic, gamma radiation, etc., in the presence of appropriate initiators. Commensurate with the scope of the present invention, such modified biocompatible materials capable of undergoing free radical polymerization have the formula:

A—X wherein A is selected from a polysaccharide, lipid, or polycation, X is a moiety containing a carbon-carbon double bond or triple bond capable of free radical polymerization; and A and X are linked covalently through linkages selected from ester, ether, thioether, disulfide, amide, imide, secondary amines, tertiary amines, direct carbon-carbon (C—C) linkages, sulfate esters, sulfonate esters, phosphate esters, urethanes, carbonates, and the like.

As employed herein, ester linkages refer to a structure for linking A to X of either

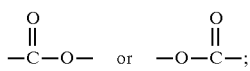

ether linkages refer to a structure for linking A to X of —O—, thioether linkages refer to a structure for linking A to X of —S—, disulfide linkages refer to a structure for linking A to X of —S—S—, amide linkages refer to a structure for linking A to X of either

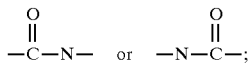

imide linkages refer to a structure for linking A to X of

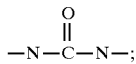

secondary or tertiary amine linkages for covalently linking A to X refer to

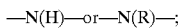

direct carbon—carbon linkages refer to a structure for linking A to X of —C—C—; sulphonate and sulphate ester linkages for covalently linking A to X refer, respectively, to

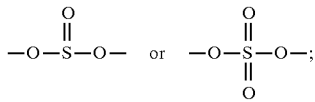

phosphate ester linkages for covalently linking A to X refer to

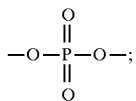

urethane linkages for covalently linking A to X refer to

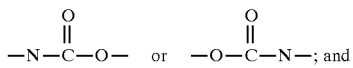; and carbonate linkages for covalently linking A to X refer to

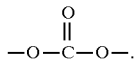.

The polymerizable moiety "X" employed in the practice of the present invention can vary widely. As a minimum, X must contain at least one carbon-carbon double bond, wherein the double bond(s) provided by X are capable of undergoing free radical polymerization. Thus, unsaturated compounds where the double bond(s) are electronically non-reactive with free radicals, or where the double bonds are sterically inaccessible to the growing polymer chain are outside the scope of the present invention. X will typically be a moiety with a backbone having in the range of about 2 up to 30 atoms. While the backbone is typically composed primarily of carbon atoms, it may also include such heteroatoms as nitrogen, sulfur, oxygen, and the like. Preferably, X will have in the range of about 2 up to 20 atoms, with a backbone having in the range of about 2 up to 10 atoms being the presently most preferred. Species such as the poly(alpha, beta-ethylenically unsaturated) isocyanates described by Nahm in U.S. Pat. No. 4,861,629, the methylol amides described by Symes et al., in U.S. Pat. No. 4,778,880, and the cinnamoyl ester described in Japanese publication J5 4128,482 (Agency of Ind. Sci. Tech.), however, are not desirable choices as sources for the radical X.

Polysaccharides and polycations are generally insoluble in organic solvents, thus limiting the ability to modify these materials. One aspect of the present invention involves the modification of these materials by covalent bonding with certain hydrophobic moieties (e.g., polyethylene glycols) which permits these materials to be solubilized in a variety of organic solvents.

Accordingly, another embodiment of the present invention is a modified biocompatible material which is soluble in organic solvents, and which is capable of undergoing free radical polymerization, said modified material having the formula:

wherein A is a polysaccharide, polycation, or lipid; X is a moiety containing a carbon-carbon double bond or triple bond capable of free radical polymerization (as described above), A and X are linked covalently as described above, Y is selected from alkylene glycols, polyalkylene glycols, or hydrophobic onium cations (e.g., tributylammonium iodide, tetrabutylammonium iodide, tetrabutylphosphonium iodide, and the like), and A and Y are linked through any one of the above described covalent linkages. In addition, where Y is an onium cation, A and Y can be linked through the following ionic bond:

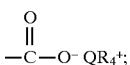

wherein Q is nitrogen or phosphorus, and R is hydrogen, an alkyl radical, an aryl radical, an alkaryl radical, or an aralkyl radical.

The process of synthesizing the polymerizable biocompatible material comprises chemically modifying biocompatible material selected from a lipid, polycation or polysaccharide having a reactive functionality thereon, and then contacting the resulting modified biocompatible material with a free radical initiating system under free radical producing conditions. Reactive functionalities contemplated include hydroxyl, carboxyl, primary or secondary amine, aldehyde, ketone or ester groups. These groups are required in order to introduce at these sites, the appropriate polymerizable substituent.

Examples of biocompatible materials include polysaccharides such as alginate, high M-content alginates, polymannuronic acid, polymannuronates, hyaluronic acid, chitosan, chitin, cellulose, starch, glycogen, guar gum, locust bean gum, dextran, levan, inulin, cyclodextran, agarose, xanthan gum, carageenan, heparin, pectin, gellan gum, scleroglucan, and the like; polycations such as polyamino acids [e.g., polyhistidine, polylysine, polyornithine, polyarginine, polyalanine-polylysine, poly(histidine, glutamic acid)-polyalanine-polylysine, poly(phenylalanine, glutamic acid)-polyalanine-polylysine, poly(tyrosine, glutamic acid)-polyalanine-polylysine, collagen, gelatin, and the like]; random copolymers of: arginine with tryptophan, tyrosine, or serine; glutamic acid with lysine; glutamic acid with lysine, ornithine, or mixtures thereof; and the like; polymers containing primary amine groups, secondary amine groups, tertiary amine groups or pyridinyl nitrogen(s), such as polyethyleneimine, polyallylamine, polyetheramine, polyvinylpyridine, and the like; and lipids such as phosphatidylethanolamine, phosphatidylserine, phosphatidylinositol, phosphatidylglycerol, dilaurylphosphatidic acid, dipalmitoyl phosphatidyl glycerol, and the like.

A primary requirement of the polymerizable substituent is the presence of moieties containing carbon-carbon double bonds (C=C) which are polymerizable with free radicals generated by suitable initiator(s) e.g., an initiator system useful for UV and visible light polymerization. Examples of moieties containing such carbon-carbon double bonds are alkenoic acids (such as acrylic acid, methacrylic acid, and the like), as well as their corresponding acid chlorides (such as acryloyl chloride, methacryloyl chloride, and the like) and corresponding acid anhydrides (such as acrylic anhydride, methacrylic anhydride, and the like), alkenols (such as allyl alcohol, and the like), alkenyl halides (such as allyl chloride, and the like), organometallic alkenyl compounds (such as vinyl magnesium bromide), and the like.

A variety of free radical initiators, as can readily be identified by those of skill in the art, can be employed in the practice of the present invention. Thus, photoinitiators, thermal initiators, and the like, can be employed. For example, suitable UV initiators include 2,2-dimethoxy-2-phenyl acetophenone and its water soluble derivatives, benzophenone and its water soluble derivatives, benzil and its water soluble derivatives, thioxanthone and its water soluble derivatives, and the like. For visible light polymerization, a system of dye (also known as initiator or photosensitizer) and cocatalyst (also known as cosynergist, activator, initiating intermediate, quenching partner, or free radical generator) are used. Examples of suitable dyes are ethyl eosin, eosin, erythrosin, riboflavin, fluorscein, rose bengal, methylene blue, thionine, and the like; examples of suitable cocatalysts are triethanolamine, arginine, methyldiethanol amine, triethylamine, and the like. A small amount of a comonomer can optionally be added to the crosslinking reaction to increase the polymerization rates. Examples of suitable comonomers include vinyl pyrrolidinone, acrylamide, methacrylamide, acrylic acid, methacrylic acid, sodium acrylate, sodium methacrylate, hydroxyethyl acrylate, hydroxyethyl methacrylate (HEMA), ethylene glycol diacrylate, ethylene glycol dimethacrylate, pentaerythritol triacrylate, pentaerythritol trimethacrylate, trimethylol propane triacrylate, trimethylol propane trimethacrylate, tripropylene glycol diacrylate, tripropylene glycol dimethacrylate, glyceryl acrylate, glyceryl methacrylate, and the like.

A particularly preferred embodiment of the present invention is a modified alginate capable of being polymerized and ionically crosslinked. Alginate may be modified so as to produce the compound A—X where A is a naturally occurring or synthetic modified form of alginate, X is a moiety containing a C=C or C≡C capable of undergoing free radical polymerization (as described above), and A and X are linked covalently as described above; or alginate can be modified so as to produce the compound Y—A—X where Y is an alkylene glycol or a polyalkylene glycol or a hydrophobic onium cation. By attaching X to alginate via the OH group thereof, or by varying the degrees of substitution of the alginate COOH group with X, a novel material can be obtained which possesses the dual capacity for undergoing both ionic and covalent crosslinking. Furthermore, increased negative charge density of this modified alginate can be achieved by sulfonation of naturally occurring or synthetic modified forms of alginate ($A_s$) Thus, $A_s$ is a novel form of alginate with increased negative charge density. This sulfonation step is possible following modification of the alginate to the form A—X as described above, resulting in a polymerizable, ionically crosslinkable, highly negatively charged form $A_s$—X; in addition, Y—A—X alginate, i.e., the organic soluble polymerizable alginate, can be further modified by sulfonation, obtaining yet another novel form of alginate designated Y—$A_s$—X.

The sequence of modification can have several variations, all resulting in novel alginate derivatives (e.g., $A_s$, A—X, $A_s$—X, Y—A—X, and Y—$A_s$—X).

A presently preferred polysaccharide of the invention is a modified alginate capable of being crosslinked by free radical polymerization, wherein the modified alginate is made by reacting a chemical compound which includes moieties containing carbon-carbon double bonds which are capable of free radical polymerization, wherein the unsaturated chemical compounds are substituted at the carboxyl or hydroxyl group of the alginate. Exemplary unsaturated chemical compounds with which the alginate is reacted include acryloyl chloride, methacryloyl chloride, acrylic acid, methacrylic acid, allyl alcohol, allyl chloride, acrylic anhydride, methacrylic anhydride, vinyl magnesium bromide, and the like. Especially preferred modified alginates are selected from an alkenyl ester of alginate, alkenyl ether of alginate or carbonyl substituted alkenyl alginate. Optionally, prior to modification of the alginate with the unsaturated chemical compound, the alginate is solubilized in an organic solvent by covalent linkage to polyethylene glycol. Examples of the resulting modified alginates include alkenyl esters of PEG-alginate, alkenyl ethers of PEG-alginate and carbonyl substituted alkenyl PEG-alginates.

In one aspect, not all carboxyl groups of the above-described alginate are substituted, therefore, the alginate may subsequently be ionically crosslinked as well as covalently polymerized. In another aspect, none of the carboxyl groups of the above-described alginate are substituted, therefore, the alginate may be subsequently ionically crosslinked as well as covalently polymerized.

The process of making microcapsules using the above-described novel biocompatible materials, e.g., the above-described forms of alginate (e.g., $A_s$, A—X, $A_s$—X, Y—A—X, and Y—$A_s$—X) result in capsules with increased stability and biocompatibility. Microcapsules could be formulated by the air-jet droplet generation technique (Lim & Sun, 1980 (22.)); by co-axial oil extrusion, or by oil emulsification. Gelling polysaccharides (such as the above-described alginate materials, A—X, Y—A—X, $A_s$—X, and Y—$A_s$—X) afford the unique ability to generate microcapsules by ionically crosslinkage using divalent cations ($Ca^{++}$, $Ba^{++}Sr^{++}$, etc.) and then polymerizing the thus formed gel bead by release of free radicals using a light source (UV, visible or laser). The capsules formed in this manner are more stable, and also provide a unique form of drug delivery vehicle whereby ionically bound drugs or drugs entrapped in the polysaccharide matrix may be leached from the gel sphere by ionic exchange or passive diffusion over a concentration gradient.

It is another embodiment of this invention to increase capsule stability by increasing ionic bond strength within the capsule core by the use of barium in combination with calcium in combination with gelling polysaccharide materials modified according to the invention to such forms as A—X, Y—A—X, $A_s$—X, Y—$A_s$—X.

Compositions of the present invention can be crosslinked so as to retain any one of a variety of forms, e.g., gels, microcapsules, macrocapsules, and the like. Gels of a variety of shapes and sizes can be prepared merely by subjecting invention compositions to ionic and/or covalent crosslinking conditions. Such gels can optionally be prepared in the presence of one or more biologically active compounds, so as to provide an immunoprotective coating for the biologically active material. Gels prepared in the absence of any specific biologically active additives are also useful for a variety of purposes, such as, for example, as a wound dressing, providing a protective barrier for injured skin.

Microcapsules prepared in accordance with the present invention comprise biologically active material encapsulated in the above-described biocompatible crosslinkable material, wherein the microcapsule has a volume in which the largest physical dimension of the capsule, including the contents thereof, does not exceed 1 mm.

Macrocapsules prepared in accordance with the present invention comprise biologically active material encapsulated in the above-described biocompatible crosslinkable material, wherein the macrocapsule has a volume in which the largest physical dimension is greater than 1mm. Macrocapsules can contain "free" (i.e., unmodified by any coating) cells or groups of cells therein. Alternatively, macrocapsules may contain cells or groups of cells which are themselves encapsulated within microcapsules.

Biologically active materials contemplated for encapsulation (to produce microcapsules or macrocapsules) according to the present invention include individual living cells or groups of living cells [such as, for example, islets of Langerhans, dopamine secreting cells (for treatment of Parkinsonism), nerve growth factor secreting cells (for the treatment of Alzheimer's disease), hepatocytes (for treatment of liver dysfunction), adrenaline/angiotensin secreting cells (for regulation of hypo/hypertension), parathyroid cells (for replacing thyroid function), norepinephrine/metencephalin secreting cells (for the control of pain)]; pharmacologically active drugs; diagnostic agents, and the like.

The invention will now be described in greater detail by reference to the following non-limiting examples.

EXAMPLE 1

Preparation Of Covalently Crosslinkable Polysaccharide (i)

Sodium alginate or alginic acid ($M_n$=175000) was dried in a vacuum oven for 24 hours at 60° C. The dry powder was suspended in dichloromethane dried with 4 A molecular sieves (acetone, benzene, toluene, and other dry organic solvents may also be used) at a concentration of 10 g in 100 ml. A two fold excess of acryloyl chloride was used (1.64 ml) and a base, triethyl amine (2.8 ml) was added to remove HCl upon formation. The reaction was carried in a round bottomed flask under argon with constant reflux for 24 hours. The reaction mixture was filtered to remove the alginate acrylate while the filtrate containing triethylamine hydrochloride was discarded. The substituted alginate was washed twice with ethanol and dried in a vacuum oven. To obtain an alginate with a lower degree of substitution, correspondingly lower amounts of acryloyl chloride were used in the reaction medium. A high G-content alginate (G content 64%) was used for the above modification scheme. Other alginates with varying G contents may be used.

EXAMPLE 2

Preparation Of Covalently Crosslinkable Polysaccharide (ii)

An alternative technique of reacting acryloyl chloride to alginate was developed in which an ionically crosslinked gel in water was subject to stepwise solvent exchange with tetrahydrofuran (THF, dimethyl sulfoxide may also be used). Alginate gel beads (approx. 400 um diameter) were sequentially transferred to solutions containing water/THF in the ratios 0.75/0.25, 0.5/0.5, 0.25/0.75, and 0/1. The beads were allowed to equilibrate in each solution for 30 minutes before being transferred to the next solution. Three exchanges with 100% THF were done to ensure removal of all water in the system. The purpose of using gel beads in the reaction was to provide a freely diffusible matrix to ensure permeability to reactants. The reaction was performed as in Example 1, the beads separated by sieving, washed with THF, and the THF then exchanged for water. The beads were then dissolved by exposure to sodium citrate at a concentration of 50 mM, and the resulting solution dialysed against deionized water for 24 hours, then freeze dried to obtain the modified alginate.

EXAMPLE 3

Preparation Of Covalently Crosslinkable Polysaccharide (iii)

The carboxyl groups on the alginate molecules were targeted for esterification by allyl alcohol. 2 g of alginate were dissolved in 100 ml of water. The solution was acidified to pH 3.2–3.5 with concentrated sulfuric acid. At this pH, approximately 50% of all the carboxyl groups on the polymer were protonated and therefore susceptible to esterification. An eight fold excess (molar basis) of allyl alcohol was added to the acidified solution and the reaction mixture refluxed overnight. The mixture was then neutralized with sodium hydroxide and added to an excess of ethanol (or tetrahydrofuran) to precipitate the product. The precipitate was washed twice with ethanol and dried in a vacuum oven. Alternately, the hydroxyl groups on alginate could be targeted for esterification by using acrylic acid. Essentially the same procedure was followed for this reaction.

The esterification reaction is an equilibrium reaction and hence does not go to completion. In order to drive the reaction toward the products, an excess of one of the reactants was used. Also, after equilibrium was reached, water formed in the reaction was continually withdrawn by allowing the mixture to boil for a few hours without refluxing.

EXAMPLE 4

Preparation Of Covalently Crosslinkable Polysaccharide (iv)—Using Organic Soluble Alginates A commercially available esterified alginate, propylene glycol alginate, is more hydrophobic and hence soluble in organic solvents like dimethylsulfoxide (DMSO), acetone, dimethyl formamide (DMF), dimethyl acetamide (DMA), etc. The reaction in Example 1 was performed using the organic soluble alginate in a homogeneous rather than a heterogeneous system. In contrast to the esterification reaction in Example 3, reaction with the acid chloride is not an equilibrium reaction and essentially goes to completion. This technique allowed for a greater control over the degree of substitution of alginate by polymerizable groups.

Other organic soluble alginates suitable for covalent attachment of polymerizable groups include the relatively hydrophobic esters prepared by the technique described by Della Valle (1987a(7.)). Della Valle describes a method of ion exchange to replace cations such as sodium in sodium alginate with large hydrophobic cations such as the tetrabutylammonium cation. The tetrabutylammonium alginate thus formed is fairly hydrophobic and may be dissolved in an organic solvent such as DMSO, DMF or DMAC. This hydrophobic salt can then be used as a reaction intermediate to produce a polymerizable alginate. Thus modified naturally occurring alginates may be used to synthesize covalently crosslinkable derivatives.

EXAMPLE 5

Preparation Of Covalently Crosslinkable Polysaccharide (v)—Inducing Solubility In Organic Solvents—Modification With Polyethylene Gly col (PEG)

PEG has the unique property of being soluble in organic solvents as well as in aqueous media. If a sufficient quantity of PEG can be covalently attached to the polysaccharide, organic solubility will result. Such a technique has been used to make the insoluble polysaccharide chitosan soluble in many solvents (Harris et al., 1984(17.)). The grafting of PEG to chitosan was through amine groups on chitosan using the PEG aldehyde derivative. The methods outlined below utilize a different chemistry. In addition to increasing organic solubility, PEG has been used to make materials more biocompatible (Desai and Hubbell, 1991(10.); Abuchowski et al., 1977(1.)). A number of chemical methods may be utilized to covalently attach PEG to alginate. These are outlined below.

A standard esterification reaction was utilized with reaction conditions similar to the one described in Example 3. PEG has hydroxyl groups (—OH) which can be esterified with the carboxyl groups (—COOH) on the polysaccharide to obtain an ester link. An excess of PEG (mol. wt. 10000 was used; other molecular weight PEGs can also be used; a monofunctional PEG such as monomethoxy PEG may also be used) was used in the reaction mixture. After 12 hours the reaction reaches equilibrium, the reaction product was precipitated in tetrahydrofuran (or other suitable solvent) and dried under vacuum. The dried product (PEG substituted polysaccharide) was reacted with acryloyl chloride according to Example 1 or 4 in organic solvent in a homogeneous system due to organic solubility afforded by attachment of PEG. A derivative of PEG, i.e., PEG carboxylic acid, prepared by the techniques described by Harris (1985(16.)) may also be esterified with hydroxyl groups on the polysaccharide to obtain its PEG derivative.

Alternatively, PEG epoxide (or glycidyl ether of PEG), obtained by the reaction of PEG with epichlorohydrin, can be reacted with a polysaccharide in basic conditions for 24 hours to achieve PEG grafting as described by Pitha et al. (1979(26.)) who bound a PEG derivative to dextran. Other alternative routes may also be conceived based on the chemistry of hydroxyl and carboxyl groups which are present on the polysaccharides. Harris (1985(16.)) has an excellent review of PEG chemistry from which alternative schemes may be derived.

Having obtained an organic soluble polysaccharide, the reaction in Example 1 may be used to make it photopolymerizable.

EXAMPLE 6

Preparation Of Covalently Crosslinkable Polysaccharide (vi) Preparation Of The Vinyl Ether A PEG-modified organic soluble alginate prepared as outlined in Example 5 was dissolved in dry dimethyl sulfoxide. A nitrogen atmosphere was maintained in the reaction vessel. The sodium salt (alkoxide) of the alginate was prepared by addition of sodium naphthalide till the green color persisted. The temperature was raised to 100° C. and acetylene gas was bubbled through the reaction vessel at a known rate. The reaction was stopped after 2 hours, the reaction mixture cooled, the vinyl substituted polymer precipitated in an excess of ether and dried in a vacuum oven. The degree of vinyl substitution varied depending on the length of reaction. This resulted in a vinyl substituent linked to the alginate through an ether linkage as opposed to the examples above which generated an ester linkage. This method was adapted from Mathias et al. (1982(23.)), who used it to synthesize divinyl ethers of oligooxyethylenes.

EXAMPLE 7

Alternative Routes For Preparation Of Covalently Crosslinkable Polysaccharide

Organic soluble alginates (e.g., PEG-alinates) may be reacted to form the alkoxide (as in Example 6) followed by addition of vinyl halides or allyl halides to produce the vinyl and allyl ethers of alginate which are readily polymerizable.

Alternately, organic soluble alginate esters after formation of the alkoxide may be reacted with Grignard reagents such as vinyl magnesium bromide or allyl magnesium bromide in scrupulously dry conditions to form the corresponding vinyl and allyl derivatives linked directly to the carbonyl carbon of the ester.

EXAMPLE 8

Synthesis of Acrylic Anhydride

Acrylic acid (0.2 mol) was reacted with aceticanhydride (0.1 mol) at a temperature of 60°–70° C. for 2 hours. Finely powdered copper (0.1 g) was added as a polymerization inhibitor. The mixture was then fraction distilled and three separate fractions collected. The first fraction gave predominantly acetic acid (a reaction product), the second fraction gave a mixture of acetic acid and acrylic acid, and the last fraction (with a boiling point of approximately 65° C. at 10 mm Hg) was predominantly acrylic anhydride. Purity of the fractions was determined by Fourier Transform Infrared Spectrometry. Yield: 60%.

EXAMPLE 9

Synthesis of Acrylate Ester of Sodium Alginate

Sodium alginate (5 g) was dissolved in 500 ml of water and cooled to 40° C. in an ice bath. Acrylic anhydride (4 ml) was added drop by drop with constant stirring to the cold alginate solution and the pH maintained at 9.0 by addition of suitable quantity of 50% NaOH. The stirring was continued for 24 hours at a temperature of 4° C. The reaction product was precipitated in 100% ethanol, filtered, washed 3 times with ethanol. The product was then dissolved in water and dialyzed against deionized water through a dialysis membrane with a molecular weight cutoff of 12000–14000 for 24 hours. The dialysed product was freeze dried to obtain the pure acrylate ester of sodium alginate. Yield: 3.5 g. The ester formation by this method was targeted to the secondary hydroxyl groups present on the monomeric units, i.e., mannuronic acid and guluronic acid present in the alginate molecule. Those of skill in the art recognize that the degree of substitution of the alginate can be varied by use of different ratios of alginate to anhydride in the above-described reaction.

EXAMPLE 10

Synthesis of Chitosan Acrylate Derivative

Chitosan (5 g) was dissolved in 500 ml of 1% acetic acid and the procedure in Example 9 was repeated to initial stages of addition of acrylic anhydride was maintained below pH 7. Chitosan has in its monomeric unit two hydroxyl groups, one of which is a primary hydroxyl and another that is a secondary hydroxyl, and a primary amino group. All of these are reactive towards the anhydride in the order of reactivity amine>primary hydroxyl>secondary hydroxyl.

EXAMPLE 11

Synthesis of Allyl Ether of Sodium Alginate

Sodium alginate (5 g) was dissolved in 500 ml of water. 2 ml of 50% NaOH were added and the mixture cooled to 4° C. in an ice bath. Allyl chloride (10 ml) was added and the mixture stirred and maintained at 4° C. for 24 hours. The reaction product was precipitated in 100% ethanol, filtered, washed 3 times with ethanol. The product was then dissolved in water and dialyzed against deionized water through a dialysis membrane with a molecular weight cutoff of 12000–14000 for 24 hours. The dialysed product was freeze dried to obtain the pure acrylate ester of sodium alginate. Yield: 3.5 g. The ether formation by this method was targeted to the secondary hydroxyl groups present on the monomeric units, i.e., mannuronic acid and guluronic acid present in the alginate molecule. As noted above, the degree of substitution can readily be varied.

EXAMPLE 12

Synthesis of Chitosan Allyl Derivative

Chitosan (5 g) was dissolved in 500 ml of 1% acetic acid and cooled to 4° C. on an ice bath. Allyl chloride (10 ml) was added and the mixture stirred and maintained at 4° C. for 24 hours. The allyl derivative of chitosan was isolated by a procedure similar to the one above in Example 11. Substitution of the allyl group is possible once again at all of the three possible sites described in Example 10. Reactivity of each site is also in the same order.

EXAMPLE 13

Increasing Charge Density Of Polysaccharides by Sulfonation

Addition of sulfonic acid (—$SO_3H$) groups to the ring structure of alginates is a method of increasing negative charge density since the acidic group is dissociated at neutral pH. This has applications in increasing the ionic crosslinking capabilities of the alginate (or other polysaccharide) resulting in a more stable gel structure.

Naturally occurring and synthetic alginates, as well as PEG-modified alginates, could be linked covalently to the sulfonic acid groups. The substitution occurs on the hydroxyls present in the alginate structure. If organic insoluble alginates are used, the reaction is heterogeneous, while a homogeneous reaction is possible with organic soluble alginates.

The alginate (natural or modified) is dissolved (or suspended) in dry dimethyl sulfoxide (or other suitable solvent). A suitable base, e.g., triethyl amine is added (to complex the liberated HCl in the reaction), along with chlorosulfonic acid, which attacks the hydroxyl groups of the alginate. The degree of substitution can be manipulated (especially in homogeneous conditions) by addition of suitable amount of chlorosulfonic acid. The reaction is typically carried out at 60°–70° C. overnight. The substituted alginate is separated by precipitation with excess ether (for organic soluble alginates) or by filtration (if organic insoluble). The product is dried in a vacuum oven.

EXAMPLE 14

Preparation Of Chemically Crosslinkable Polycations

Polycations such as polylysine, polyornithine, polyethyleneimine, polyetheramine, polyamideamine, polyvinylpyridine, etc., may be modified to make them photopolymerizable. All the above mentioned polycations have primary or secondary amine groups in their structures. Acid chlorides like acryloyl chloride react readily with amines to form an amide linkage (Morrison and Boyd, 1973(25.)). The polycations were mostly obtained in their salt form (hydrochloride or hydrobromide) which were water soluble. A number of these polycations are insoluble in organic solvents. Reactions to make the polycations polymerizable can be carried out in aqueous medium by reaction with anhydrides, employing the same method described above for polysaccharides. The reactions can also be carried out in organic solvents if the polycations are first modified to render them organic soluble. In order to solubilize them in organics and thereby facilitate a reaction with acryloyl chloride to produce a polymerizable derivative, they were reacted with PEG.

Several techniques could be used for covalent attachment of PEG to the amine groups on the polycations. One technique used was the activation of PEG with 1,1-carbonyldiimidazole (CDI). This involved the dissolution of vacuum dried PEG in dry dichloromethane (or other solvent) and addition of CDI. The reaction was carried at room temperature overnight, followed by precipitation of the PEG derivative in ether. The derivative was dried under vacuum. Grafting of CDI activated PEG to polylysine was performed in aqueous borate buffer at pH 9 for 24 hours. The reaction mixture was dialyzed against deionized water for 24 hours and the resultant solution freeze-dried to obtain the PEG grafted PLL. The graft copolymer was dissolved in a suitable solvent and reacted with acryloyl chloride (as in Example 1) to obtain the polymerizable product.

Other derivatives of PEG that react with amine groups may also be utilized. Examples of such derivatives are described in the paper by Harris (1985(16.)).

EXAMPLE 15

Preparation Of Chemically Crosslinkable Lipids

Lipids used in the formation of liposomes such as phosphatidylethanolamine, phosphatidylserine, phosphatidylinositol, phosphatidylglycerol, dilaurylphosphatidic dipalmitoylphosphatidyl glycerol, etc., have in their structures a hydroxyl group or an amine group which can be reacted to acryloyl chloride or other suitable agent to make these lipids photocrosslinkable. The general method for this reaction is described in Example 1. The preparation of a crosslinkable lipid would greatly enhance the stability of liposomes in physiological conditions. These lipids can be rendered polymerizable by the same methods described above for polysaccharides and polycations. PEG could also be attached to these lipids to enhance their solubility in organic solvents and thereby facilitate the reaction with acryloyl chloride. The attachment of PEG was done by the method outlined in Example 5 and then followed by reaction with acryloyl chloride.

EXAMPLE 16

Laser/Visible Light Photonolymerization To Produce Polysaccharide Gels And Microspheres In recent years considerable interest has been expressed in the use of lasers for polymerization processes (Wu, 1990 (31.)). These polymerizations are extremely fast and may be completed in milliseconds (Decker and Moussa, 1989(6.); Hoyle, et al., 1989(18.); Eaton, 1986(13.)). It was desired to use these techniques for the formation of covalently crosslinked alginate microcapsules containing pancreatic islets. Substituted alginates prepared by the techniques outlined in Examples 1 through 7 and 9 through 13 were dissolved in aqueous bicarbonate buffered saline (or other buffer) at pH 7.4 at a concentration of 0.1–10% (w/v). A free radical initiating system comprising a dye and a cocatalyst were used to initiate polymerization. The dye (ethyl eosin; 0.01 µM up to 0.1M), a cocatalyst (triethanolamine; 0.01 µM up to 0.1M), and comonomer, which increases the rate of polymerization (vinyl pyrrolidinone; 0.001 to 10%) were added to the solution, which was protected from light until the photopolymerization was carried out.

Two different techniques to produce microspheres were used: one involved emulsification with an oil (silicone oil) and the second was a coaxial extrusion from a hypodermic needle (20 G to 26 G) with the monomer solution surrounded by a sheath of flowing silicone oil in glass tubing. The resultant microspheres were exposed to laser radiation from an argon ion laser at a wavelength of 514 nm at powers between 10 mW to 3 W. An exposure time as low as 100 msec was found to be adequate for polymerization and microsphere formation. Photopolymerization may also be performed with a mercury arc lamp which has a fairly strong emission around 514 nm. Visible radiation between wavelengths of 400–700 nm have been determined to be nontoxic to living cells (Karu, 1990(20.); Dupuy et al., 1988(12.)). The use of wavelength specific chromophores as polymerization initiators ensured that they were the only species in the polymer/cell suspension that absorbed the incident radiation.

Polycations and lipids may also be photopolymerized using this technique.

EXAMPLE 17

UV Photopolymerization To Produce Polysaccharide Gel And Microspheres

A different initiating system from the one employed in Example 16 was used to produce alginate gels. A UV photoinitiator, 2,2-dimethoxy-2-phenyl acetophenone, was added to a solution of substituted alginate (prepared as described in any one of Examples 1 through 7 or 9 through 13) in aqueous buffer at a concentration of 1000–1500 ppm. This solution was exposed to long wave UV radiation from a 100 watt UV lamp. The time required for gellation varied between 5 to 20 seconds depending on the concentrations of initiator and addition of other polymerizable comonomers such as vinyl pyrrolidinone (0.001 to 10%). Gel microspheres could be prepared, for example, by the emulsification technique described in Example 19. The short-term exposure of islet cells to long wave UV radiation was determined to have no cytotoxicity. A UV laser may also be used for the photopolymerization.

Polycations and lipids can also be photopolymerized using this technique.

EXAMPLE 18

Visible Light Photopolymerization of Alginate and Chitosan Derivatives

The polysaccharide derivatives prepared by the techniques outlined above were dissolved in water at a concentration of 2%. A photoinitiator (ethyl eosin; 0.01 µM to 0.1M), a cocatalyst (triethanolamine; 0.01 µM to 0.1M), and optionally, comonomer (1-vinyl 2-pyrrolidinone; 0.001 to 10%, when present) were added to the solution, which was protected from light until the photopolymerization reaction was carried out.

A small quantity of the prepared solution was placed in a test tube and exposed to visible radiation either from an argon ion laser at a wavelength of 514 nm at powers between 10 mW to 3 W, or a 100 watt mercury arc lamp which has a fairly strong emission around 514 nm. The gelling time was noted and found to be extremely rapid with the laser (order of milliseconds for acrylate derivatives) and fairly rapid with the mercury lamp (order of seconds for acrylate derivatives) and varied with the concentrations of polymer initiator, cocatalyst, and comonomers in the system.

In general the gelling time of the acrylate derivatives (in order of seconds) was faster than that of the allyl derivatives (order of minutes).

EXAMPLE 19

Emulsification Technique To Produce Microcapsules

Islets were suspended in a polymerizable mixture of alginates containing the appropriate initiating systems as described in Examples 16 and 17 above at a concentration of approximately 5000–15000 islets per ml. The well mixed suspension was added into a sterile vessel containing sterilized medical grade silicone oil (Dow Corning) and emulsified by rapid stirring. This resulted in the formation of spherical droplets of polymerizable solution containing islet cells. The stirring suspension was exposed to either visible light (from a high pressure Hg lamp, or a laser) or to UV light depending on the initiating system used. Gellation of the droplets to form microcapsules occurred rapidly, typically in less than 30 seconds. An aqueous physiologic buffer was added to the oil and the microcapsules preferentially partitioned into the aqueous phase. The aqueous phase was separated in an apparatus similar to a separating funnel and the microcapsules transferred to culture medium.

EXAMPLE 20

Extrusion In A Two Phase Coaxial Flow System

A coaxial flow system designed to polymerize droplets containing cells such as islets (to form microcapsules) has been described in the literature (Dupuy et al., 1988(12.)). This device allows the droplets containing cells to be polymerized as they are formed. The body of the device is fabricated from borosilicate glass. The apparatus comprises a needle, preferably a hypodermic needle through which a monomer or cell suspension is introduced. A port is the entrance for the shear fluid, which is silicone oil in the preferred embodiment. A stopper for the device body may be pressure fitted or in the preferred embodiment screwed into the device housing. A compressible seal, which is preferably a silicone rubber sealing plug, is provided for an airtight closure. The housing may be a glass housing capable of permitting the transmission of light, specifically laser light therethrough. Alternatively, the housing may be light opaque if it is provided with a light transmitting window so that the coated cells can be exposed to laser light transmitted through the window.

The cell suspension is injected through a hypodermic needle of appropriate gauge into a flowing silicone oil stream that surrounds the needle. Droplets form as a result of surface tension effects and droplet size may be controlled by appropriate selection of needle size, and flow rates of oil and aqueous (cell suspension) phases. The droplets form in the vicinity of the injection point by breaking off from a jet of the polymer solution containing the islets (or other cell type) and flowing into a narrow glass capillary which serves as a window for incidence of a narrow (0.5–5 mm diameter) laser beam. As the droplet passes through the laser beam, rapid gellation occurs as a result of free radical generation due to presence of appropriate light absorbing dyes and cocatalysts and a polymeric crosslinked capsule is formed around the cells. The exposure time is very short, of the order of milliseconds and can be accurately manipulated by adjusting the flow rate of the oil phase. That the microcapsules in oil are collected in a vessel and separated as described in Example 13 above.

A piezoelectric transducer may be attached to the needle assembly to vibrate the needle at a known frequency. This enable the formation of small droplets of controlled size.

EXAMPLE 21

Capsule Formation Using Ionic And Covalent Crosslinking

The polymerizable alginate generated by any of the techniques outlined above is a material having the capacity to be ionically crosslinked, while simultaneously, covalent crosslinking is also possible. This unique property of the modified alginate facilitates the generation of a microcapsule by the conventional process (extrusion through a needle with a coaxial air stream) of ionic crosslinking in a solution containing multivalent cations. Microcapsule formation is carried out under very mild entrapment conditions, which is highly desirable for handling biologically active materials. Polymer can be readily concentrated in a spherical form about a core of entrapped biologically active material (by ionically crosslinking the polymer, without the need for emulsification, with consequent exposure of the biologically active material to oils, etc.). Further crosslinking of the capsule (by free radical initiated polymerization) can then be carried out on the "pre-formed" capsule, thereby imparting additional strength to the capsule.

The ionically crosslinked alginate can simultaneously or subsequently be photocrosslinked (i.e., covalently crosslinked) by exposing the ionically crosslinked alginate containing a suitable concentration of dissolved photocatalysts (e.g., ethyl eosin; 0.1 $\mu$M–0.1M, triethanol amine; 0.01 $\mu$M,–0.1M, and optional comonomers, e.g., vinyl pyrrolidinone, 0.001–10%) to initiating irradiation, e.g., as provided by a high pressure mercury lamp. Alternatively, the alginate solution containing photocatalysts can be covalently crosslinked first by exposure to suitable light source, then ionically crosslinked by exposure to a solution of multivalent cations such as calcium. In the formation of microcapsules, one or both of the components of the photoinitiating system can be included in the bath providing the source of multivalent cations; or the ionically crosslinked gels can be transferred to a bath containing dissolved photocatalysts which are then allowed to diffuse into the ionically crosslinked gel while being exposed to the initiating light source. By controlling the immersion time of the capsules in the photoinitiator-containing solution, and thereby controlling the depth of penetration of initiators into the capsule (as a result of diffusion), during exposure to the light source, or following exposure to the light source, varying thicknesses of a polymerized shell on the microcapsules can be achieved. If desired, the ionically crosslinked core can be degelled without disrupting the capsule by exposure of the polymerized capsules to a buffered citrate solution. Preferred concentration ranges for the various components of the photoinitiating system are ethyl eosin (5 $\mu$M–0.5 mM), triethanolamine (5 mM–0.1M), and 0.01–1% for comonomers (e.g., vinyl pyrrolidinone).

The unique dual property of this material, i.e., ionic and covalent crosslinkability, allows the encapsulation of living cells to be carried out in a very gentle environment, which ensures that capsule integrity can be maintained in an in vivo environment.

EXAMPLE 22

Dual Crosslinking Nature of Alginate Acrylates

The unique dual ability of invention compositions to undergo ionic as well as covalent crosslinking is demonstrated herein employing the alginate acrylate prepared as described in Example 9. Thus, a solution of alginate acrylate (2 wt%) in water with appropriate concentration of photoinitiators as described above was injected through a syringe into a bath containing calcium ions. Droplets of the alginate were immediately gelled by calcium ions on contact with the solution. The droplets were simultaneously exposed to visible radiation in the range of 500–550 nm from a 100 watt mercury lamp with a bandpass filter. The beads were exposed to the radiation for one minute following which they were transferred to a solution containing sodium citrate (1M). Unmodified alginate gels produced by crosslinking with calcium only are rapidly dissolved in a solution containing citrate because of its calcium chelating properties. However, the alginate acrylate photopolymerized gelled beads remained indefinitely stable in this solution, indicating the presence of covalent crosslinks as the result of polymerization. These covalent crosslinks help maintain the integrity of the gel despite the reversal of the ionic crosslinks by calcium chelation.

EXAMPLE 23

Variation Of Crosslink Density For Permeation Control Of Diffusible Species Through Polysaccharide Gels Alginates from Examples 1 through 7 and 9 through 13 can be produced at varying levels of substitution of crosslinkable groups. Depending on the average distance between substitutions on the alginate polymer chain, a mean 'pore size' can be computed for the crosslinked alginate gel. Thus a high level of substitution would imply a small pore size or a low molecular weight cutoff, and vice versa. FITC-dextrans of varying molecular weights were immobilized in crosslinked alginate gels and the permeability of various formulations tested by measuring the release of dextran into the bulk solution. It was possible to design an alginate gel with a given permeability characteristic by varying the level of substitution of polymerizable groups on the alginate polymer.

EXAMPLE 24

Polysaccharides With Dual Ionic And Covalent Crosslink Capabilities For Drug Release The level of substitution of polymerizable groups targeted at the carboxyl group on alginates could be controlled by addition of suitable quantities of these reagents. This would result in an alginate with some carboxyl groups that were substituted with polymerizable moieties and available for covalent crosslinking, while the remainder would be available for ionic crosslinking. This resulted in a material that had the unique dual properties of being able to ionically crosslink and at the same time being able to polymerize to generate covalent crosslinks. In addition to applications in cell encapsulation, applications of such a material could be quite extensive as a drug delivery system wherein the drug was ionically bound to the alginate or merely dissolved or dispersed while the matrix was covalently crosslinked and hence insoluble. Drug release would occur by exchange of the drug under physiological conditions with cations that diffused into the gel matrix or by simple diffusion across a concentration gradient.

Polymerizable substituents that were targeted selectively to the hydroxyl groups while leaving the carboxyls available for ionic linkage would be as effective, if not more effective than the carboxyl substituted alginates.

EXAMPLE 25

Encapsulation Of Cells In Photocrosslinked Polysaccharide Gels—Treatment Of Enzyme/ Hormone/Protein Deficiency States Pancreatic Islets for Diabetes: Pancreatic islets isolated and purified by techniques described elsewhere (Soon-Shiong et al., 1990(29.); Lanza et al., 1990(21.)) were added to the photocrosslinkable alginate solution containing dissolved photocatalysts in physiological buffer (as in Example 16) at a concentration of 5000–15000 islets per ml. The islet suspension was then extruded in coaxial flow with air into a solution of calcium ions, or extruded in coaxial flow with oil or emulsified in oil to produce droplets of alginate containing islets.

The droplets were rapidly photocrosslinked by exposure to a laser source or arc lamp to produce insoluble microspheres varying in size between 200 to 1000 um depending on the hydrodynamic conditions for droplet formation. The size and shape of the microspheres is dependent upon the extrusion rate and extruding capillary diameter. The encapsulated islets were put into culture and tested for viability and function to prove the innocuous nature of the polymerization.

As discussed above, several other disease states can also be treated by encapsulation of the appropriate cell types.

EXAMPLE 26

A Retrievable System For Implanted Microcapsules

Microcapsules generated by any of the techniques described above are difficult to retrieve following peritoneal implantation due to their small size (few 100 microns). A typical dosage in a dog involves the implantation of approximately 30 ml of capsules which number in thousands. A retrievable system for microcapsules would be a macrocapsule (not necessarily spherical) containing within it a therapeutic dosage of microcapsules. Such a macrocapsule could be fabricated from alginates and any of its derivatives describe above. The microcapsules are suspended in an alginate solution that may be gelled ionically or covalently, or both, in order to obtain a gelled alginate (the macrocapsule) containing within it, the microcapsules. Such a system of delivery is readily retrievable due to its physical dimensions. An example of such a system would be a long thread of gelled alginate (the macrocapsule) containing within it, the macrocapsules. The suspension of microcapsules in a crosslinkable (ionically or covalently) alginate solution could be extruded through a syringe and the outflowing jet or cylindrical stream immediately gelled either ionically or by photopolymerization. Dually crosslinkable alginates may also be utilized in which the first step would involve extrusion into a solution containing calcium ions (or other multivalent ions) followed by polymerization very similar to that described in Example 15 above. Anyone skilled in the art will recognize that retrievable systems for implanted cells or microcapsules could be devised using modified polysaccharides other than alginates, as well as modified polycations and lipids.

EXAMPLE 27

Drug/Enzyme Release From Polysaccharide Gels With Controlled 'Pore Sizes'

By controlling the degree of substitution of crosslinkable groups on the alginate molecule it is possible to taylor a 'pore size' within the crosslinked gel. Knowing the molecular dimensions of drugs and enzymes that may have therapeutic use, one could very easily synthesize an alginate gel that would release the drug/enzyme molecules at a desired rate. Examples of drug/enzyme/hormone therapy could include the treatment of hemophilia by a sustained release of Factor VIII which is deficient in hemophiliacs; the sustained release of human growth hormone; the sustained release of thyroid supplements or substitutes in patients that have undergone thyroidectomies; the sustained release of adrenal supplements or substitutes for replacement of adrenal function; the sustained release of estrogen for birth control.

EXAMPLE 28

Effects Of Systemically Delivered Chemotherapeutic Agents On Encapsulated Cells And Tissues The treatment of several diseases requires the in vitro culture of biopsied cells to test the effects of drugs that constitute potential treatments. Culturing these cells often takes several days and often, weeks may pass before an effective drug is found that affects the cultured cells in the desired fashion. A quick substitute to this technique may be the encapsulation of these cells and subsequent implantation in animals. These animals would then be treated or screened with a variety of drugs/chemotherapeutic agents and a more realistic in vivo picture of the toxicity and efficacy of these drugs on the encapsulated cells may be obtained by examining these cells following retrieval from the animal. Such in vivo assessments cannot be performed without the benefits of immunoisolation afforded by the encapsulation technology. A variety of tumor cells may be treated using this technique.

EXAMPLE 29

Chemical Modification Of Other Naturally Occurring Polysaccharides

Hyaluronic acid (HA) has recently provoked much interest in the biomedical and pharmaceutical industries. Esterified HA has been used for drug delivery (Della Valle, 1987b(8.)) and HA crosslinked with polyhydric alcohols has been used in the preparation of surgical articles (Della Valle, 1988(9.)). Debelder and Malson (1988(5.)) have described the crosslinking of HA with polyfunctional reagents, such as diepoxides, to produce water-swelling and biodegradable materials for surgical implants and the prevention of post-surgical adhesions. HA could be modified using the same techniques outlined in Examples 1–7 and 8–13 to produce a rapidly photocrosslinkable gel.

EXAMPLE 30

Polysaccharides For Use As Bioadhesives

Alginates or HA when polymerized or crosslinked on a tissue, adhered to the tissue on the contact side while remaining nonadhesive and 'slippery' on the air side. This was probably due to intimate contact and mixing between the mucus layer on the tissue and the polysaccharide in solution. It was found that when tissues were brought together in close proximity and the polysaccharide gelled in contact with both tissues, a firm adherence was obtained. Vascular anastomoses and bowel anastomoses performed in rats using these gels showed complete healing in 2–3 weeks with no problem of leakage or mechanical failure. Another use of the gels as an adhesive would be in ophthalmic use. Eye surgery often requires incision of the cornea. In wound closure, instead of suturing, the corneal incision could be closed using the polymerizable alginates. This 'bandage' would be slippery and cause a greatly reduced degree of discomfort that results from sutures.

EXAMPLE 31

Photocrosslinked Hyaluronic Acid In The Prevention Of Postoperative Adhesions Postoperative adhesions, or filmy connective or scar tissue bridges formed during the normal healing process following surgery, often result in bowel obstructions and infertility arising from kinking of fallopian tubes following abdominal surgery. The isolation of wounded tissue (as a result of surgery) by use of a physical barrier between this tissue the and the surrounding organs has been shown to alleviate these problems. HA has been used previously for this purpose, albeit in a soluble form. As expected, even fairly viscous solutions of HA are likely to dissolve away resulting in the eventual formation of adhesions. The use of in situ photopolymerization of HA resulting in the formation of a cohesive gel around the injured tissue is likely to efficiently isolate the injured tissue from surrounding organs and thus prevent the formation of adhesions.

EXAMPLE 32

Photocrosslinked Alginate and Chitosan Gel Compositions for use in Wound Healing Wounds that involve broken or damaged skin run the risk of becoming infected with airborne or waterborne bacteria and may result in improperly healed wounds in the mild cases to life threatening problems in severe cases such as burns. In addition to the risk of infection, excessive loss of moisture from the wound may also result in poor healing. As is well known, severe burns are excruciatingly painful for a patient, and can present severe and even life threatening problems if the burned skin sloughs off exposing subdermal layers. In this context it is desirable to provide a dressing or covering which would in effect form a substitute "skin" for the patient. This would require that the dressing "breathe" or have adequate air permeability characteristics. At the same time it is desirable that the proper moisture conditions be maintained for prompt healing of burned skin; for example, an appropriate dressing must not absorb excessive moisture and thus dry the wound, inasmuch as this will inhibit proper healing. In addition, pharmacologically active agents may be impregnated into the dressing which upon release at the wound site may stimulate the healing process.

Alginate and chitosan have been previously used in wound dressing. Chitosan is known to have a stimulatory effect on cell growth. We have demonstrated in the past that alginates containing higher percentages of β-D mannuronic acid (high M-content) are cytokine stimulatory while those containing higher fractions of α-L guluronic acid residues (G-content) do not induce cytokines responsible for fibroblast proliferation [Soon-Shiong, 1991(30.)]. While the high G-content alginates are useful in cell encapsulation, the high M-content alginates help stimulate wound healing. Polysaccharides such as alginates and chitosan modified with polymerizable groups have applications as crosslinked gel dressings for wound healing. By polymerizing these materials along with suitable monomers a variety of gel types in terms of varying physical properties may be obtained ranging from soft and sticky to hard and tough for use in a variety of wound healing applications.

Alginates having very high percentages (>90%) of mannuronic acid residues (high M-content) are very effective in promoting cell proliferation through cytokine stimulation. This effect is of great potential benefit in a variety of applications, such as wound healing, as well as in the treatment of sepsis in internal or external wounds. According to the "egg-box" model for crosslinking with multivalent cations (see Smidsrød and Skjak-Bræk, 1990(28.)), the ionically crosslinking residues in an alginate are predominantly the guluronic acid residues. Thus, polymannuronic acid or polymannuronates, i.e., alginates with high M-content, have poor gelling properties when exposed to multivalent cations. Consequently, such alginates do not form stable gels with properties useful for such applications as the preparation of wound healing products. Accordingly, the preparation of a polymerizable alginate having a high polymannuronic acid or polymannuronate content would be desirable for numerous applications. Such a crosslinkable material can be prepared by imparting the ability to undergo free radical initiated crosslinking to high polymannuronic acid or high polymannuronate content materials employing the methods of the present invention.

Several monomers were used for copolymerization with the acrylate derivatives of alginate and chitosan. As examples are acrylamide (AA), acrylic acid, allyl digylcol carbonate, ethylene glycol diacrylate, glyceryl acrylate, methylene bisacrylamide (MBA), polyethylene glycol diacrylate, hydroxyethyl acrylate, hydroxethyl methacrylate, sodium acrylate, vinyl pyrrolidinone, vinyl pyridine, etc. Photopolymerization with the above described photocatalysts is the presently preferred technique of polymerization for the production of crosslinked gels, although those of skill in the art are aware that there are a plethora of techniques available for this purpose, one example of which is thermal polymerization using potassium persulfate as the initiator. The following table relates compositions of polymerized gels with corresponding physical properties.

| Alginate Acrylate (g) | AA (g) | Water (g) | Glycerol (g) | MBA (g) | Physical Property |
|---|---|---|---|---|---|
| 0.1 | 0.1 | 3.75 | 1.25 | 0.01 | fragile, soft, slippery |
| 0.1 | 0.5 | 3.75 | 1.25 | 0.01 | fragile, elastic |
| 0.1 | 1.0 | 3.75 | 1.25 | 0.01 | elastic, sticky |
| 0.1 | 1.5 | 3.75 | 1.25 | 0.01 | elastic, sticky, pliable |
| 0.1 | 2.0 | 3.75 | 1.25 | 0.01 | elastic, sticky, strong |
| 0.1 | 3.0 | 3.75 | 1.25 | 0.01 | strong, mildly elastic |
| 0.1 | 5.0 | 3.75 | 1.25 | 0.01 | strong, tough |

In the above example, only the amount of acrylamide is varied. The relative amounts of water, glycerol, and MBA may also be varied to change the physical properties of resultant gels. Similar gels were prepared from chitosan acrylate, alginate methacrylate, chitosan methacrylate, and allyl ethers of alginate and chitosan. Gels of these materials were prepared as flat sheets that could be applied to a wound. The sticky materials were tacky enough to remain bonded to skin surrounding a wound, while other materials could be adhered to a wound by means of an adhesive or by using a backing that provided adhesion around the wound site.

While the invention has been described in detail with reference to certain preferred embodiments thereof, it will be understood that modifications and variations are within the spirit and scope of that which is described and claimed.

REFERENCES

1. Abuchowski et al., 1977; "Alteration of Immunological Properties of Bovine Serum Albumin by Covalent Attachment of Polyethylene Glycol"; *J. Biol. Chem.* 252:3578–3581
2. Braun et al., 1985; *Biomed. Biochem.* Acta 44:143
3. Chang, 1984 "Microencapsulation and Artificial Cells"; Humana Press, Clifton, N.J., pp. 4–26
4. Darqy and Reach, 1985 "Immunoisolation of pancreatic B cells by microencapsulation"; *Diabetologia* 28:776–780
5. Debelder and Malson, 1986; EP Pat. No. 190215
6. Decker and Moussa, 1989; *Macromolecules* 22:4455
7. Della Valle, 1987; EPA (to Fidia, SpA) 0216453-$A_2$
8. Della Valle, 1987; EPA (to Fidia, SpA) 0251905-$A_2$
9. Della Valle, 1987; EPA (to Fidia, SpA) 0265116-$A_2$
10. Desai and Hubbell, 1991 "Solution technique to incorporate polyethylene oxide and other water-soluble polymers into surfaces of polymeric biomaterials"; *Biomaterials* 12:144–153
11. Dupuy et al., 1987 "Agarose Beads in Paraffin Oil as Interfaces to Encapsulate Living Cells. Tests of function with Islets of Langerhans"; *Artif. Organs* 11:314
12. Dupuy et al., 1988 "In situ polymerization of a microencapsulating medium round living cells"; *Journal of-Biomedical Materials Research* 22:1061–1070
13. Eaton, 1986; *Advances in Photochemistry* 13:427
14. Gharapetian et al., 1986 "Encapsulation of Viable Cells Within Polyacrylate Membranes"; *Biotech. Bioeng.* 28:1595
15. Goosen et al., 1985 "Optimization of Microencapsulation Parameters: Semipermeable Microcapsules as a Bioartificial Pancreas"; *Biotechnol. Bioeng.* 27:146–150
16. Harris, 1985 "Laboratory Synthesis of Polyethylene Glycol Derivative"; JMS-Rev. *Macromol. Chem. Phys.* C25(3):325–373
17. Harris et al., 1984; *J. Polym. Sci. Polym. Chem. Ed.* 22:341
18. Hoyle et al., 1989 "Laser-Pulsed Photopolymerization of Methyl Methacrylate: The Effect of Repetition Rate"; *Macromolecules* 22:3866–3871
19. Iwata et al., 1989 "Evaluation of Microencapsulated Islets in Agarose Gel as Bioartificial Pancreas by Studies of Hormone Secretion in Culture and by Xenotransplantation"; *Diabetes* 38:224–225
20. Karu, 1990 "Effects of Visible Radiation on Cultured Cells"; *Photochem. and Photobiol.* 52:1089
21. Lanza et al., 1990 "Large-Scale Canine and Human Islet Isolation Using a Physiological Islet Purification Solution"; *Diabetes* 39:309A
22. Lim and Sun, 1980 "Microencapsulated Islets as Bioartificial Endocrine Pancreas"; *Science* 210:908–910
23. Mathis et al., 1982; *J. Polym. Sci., Polym. Lett. Ed.* 20:473
24. Moe et al., 1991; *Food Hydrocolloids* 5:119
25. Morrison and Boyd, 1973; Organic Chemistry, Allyn and Bacon, Boston, pp. 755
26. Pitha et al., 1979 "Detergents Linked to Polysaccharides: Preparation and Effects on Membranes and Cells"; *Eur. J. Biochem.* 94:11–18
27. Sefton et al., 1990 "A HEMA-MMA COPOLYMER FOR THE MICROENCAPSULATION OF MAMMALIAN CELLS"; *Polymer Preprints* 31:217–218
28. Smidsrød and Skjåk-Braek, 1990 "Alginate as immobilization matrix for cells"; *Trends in Biotechnology* 8:71–78
29. Soon-Shiong et al., 1990 "Islet Purification by a Novel Immunomicrosphere Cell Depletion Technique"; *Transplantation Processings* 22(2):780–781
30. Soon-Shiong et al., 1991 "An Immunologic Basis for the Fibrotic Reaction to Implanted Microcapsules"; *Transplantation Proceedings* 23(1) :758–759
31. Wu, 1990; Laser Focus World, Nov. 1990, pp. 99

We claim:

1. Macrocapsules comprising biologically active material encapsulated in an ionically and covalently crosslinked biocompatible material, wherein said material, prior to being crosslinked, has the formula:

A—X wherein:

A is a polysaccharide, polycation or lipid;

X is a moiety capable of forming a covalent crosslink; and

A and X are linked covalently through linkages selected from the group consisting of ester, ether, thioether, disulfide, amide, secondary amines, tertiary amines, direct C—C linkages, sulfate esters, sulfonate esters, phosphate esters, urethanes, and carbonates, and wherein at least one physical dimension of said macrocapsule is greater than 1 mm.

2. The macrocapsules of claim 1 further comprising individual cells or groups of cells.

3. A drug delivery system comprising the macrocapsules of claim 1.

4. The macrocapsules of claim 1, wherein A is a polysaccharide selected from the group consisting of alginate, high M-content alginate, polymannuronic acid, polymannuronate, hyaluronic acid, chitosan, chitin, cellulose, starch, glycogen, guar gum, locust bean gum, dextran, levan, inulin, cyclodextrin, agarose, xanthan gum, carageenan, heparin, pectin, gellan gum, and scleroglucan.

5. The macrocapsules of claim 4, wherein said polysaccharide is sulfonated.

6. The macrocapsules of claim 1, wherein A is a polycation selected from the group consisting of polyhistidine, polylysine, polyornithine, polyarginine, polyalanine-polylysine, poly(histidine, glutamic acid)-polyalanine-polylysine, poly(phenylalanine, glutamic acid)-polyalanine-polylysine, poly(phenylalanine, glutamic acid)-polyalanine-polylysine, poly(tyrosine, glutamic acid)-polyalanine-polylysine, collagen, gelatin; random copolymers of: arginine with tryptophan, tyrosine, or serine; glutamic acid with lysine; glutamic acid with lysine, ornithine; and mixtures of any two or more thereof.

7. The macrocapsules of claim 1, wherein A is a lipid selected from the group consisting of phosphatidylethanolamine, phosphatidylserine, phosphatidylinositol, phosphatidylglycerol and dilaurylphosphatidic acid.

8. The macrocapsules of claim 1, wherein said crosslinked biocompatible material is produced by subjecting said biocompatible material to ionic crosslinking and free radical polymerization conditions.

9. The macrocapsules of claim 1, wherein A has a reactive functionality thereon and X is a reactive species capable of free radical polymerization.

10. The macrocapsules of claim 9, wherein said reactive functionality is a hydroxyl, carboxyl, primary or secondary amine, aldehyde, ketone or ester group.

11. The macrocapsules of claim 9, wherein said reactive species is an alkenoic acid or the corresponding acid chloride or acid anhydride, alkenol, alkenyl halide or organometallic alkenyl compound.

12. The macrocapsules of claim 11, wherein said reactive species is an alkenoic acid anhydride.

13. The macrocapsules of claim 9, wherein said reactive species is an acryloyl chloride, methacryloyl chloride, acrylic acid, methacrylic acid, acrylic anhydride, methacrylic anhydride, allyl alcohol, allyl chloride, or vinyl magnesium bromide.

14. The macrocapsules of claim 1, wherein said biologically active material is:

individual living cells or groups of living cells;

at least one pharmacologically active drug; or at least one diagnostic agent.

15. The macrocapsules of claim 14, wherein said living cells comprise islets of Langerhans.

16. The macrocapsules of claim 14, wherein said cells are encapsulated within microcapsules wherein the largest physical dimension of each microcapsule does not exceed 1 mm.

17. The macrocapsules of claim 1, wherein A is further linked to Y, wherein Y is an alkylene glycol, polyalkylene glycol, or hydrophobic onium cation, wherein the linkage between Y and A is selected from the group consisting of the covalent linkages ester, ether, thioether, disulfide, amide, secondary amines, tertiary amines, direct C—C linkages, sulfate esters, sulfonate esters, phosphate esters, urethanes, and carbonates; or, when Y is an onium cation, said linkage between Y and A is the ionic linkage

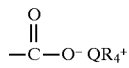

wherein Q is nitrogen or phosphorus, and R is hydrogen, an alkyl radical, an aryl radical, an alkaryl radical, or an aralkyl radical.

18. The macrocapsules of claim 17, wherein A is a polysaccharide selected from the group consisting of alginate, high M-content alginate, polymannuronic acid, polymannuronate, hyaluronic acid, chitosan, chitin, cellulose, starch, glycogen, guar gum, locust bean gum, dextran, levan, inulin, cyclodextrin, agarose, xanthan gum, carageenan, heparin, pectin, gellan gum, and scleroglucan.

19. The macrocapsules of claim 18, wherein said polysaccharide is sulfonated.

20. The macrocapsules of claim 17, wherein A is a polycation selected from the group consisting of polyhistidine, polylysine, polyornithine, polyarginine, polyalanine-polylysine, poly(histidine, glutamic acid)-polyalanine-polylysine, poly(phenylalanine, glutamic acid)-polyalanine-polylysine, poly(phenylalanine, glutamic acid)-polyalanine-polylysine, poly(tyrosine, glutamic acid)-polyalanine-polylysine, collagen, gelatin; random copolymers of: arginine with tryptophan, tyrosine, or serine; glutamic acid with lysine; glutamic acid with lysine, ornithine; and mixtures of any two or more thereof.

21. The macrocapsules of claim 17, wherein A is a lipid selected from the group consisting of phosphatidylethanolamine, phosphatidylserine, phosphatidylinositol, phosphatidylglycerol and dilaurylphosphatidic acid.

22. The macrocapsules of claim 17, wherein said crosslinked biocompatible material is produced by subjecting said biocompatible material to ionic crosslinking and free radical polymerization conditions.

* * * * *